United States Patent [19]
Dobkin

[11] Patent Number: 5,643,217

[45] Date of Patent: Jul. 1, 1997

[54] SURGICAL ATTACHMENT DEVICE

[76] Inventor: William R. Dobkin, 6020 Lido La., Long Beach, Calif. 90803

[21] Appl. No.: 373,634

[22] Filed: Jan. 17, 1995

Related U.S. Application Data

[63] Continuation of Ser. No. 369,010, Jan. 5, 1995, abandoned.

[51] Int. Cl.$^6$ .................................................. A61M 5/14
[52] U.S. Cl. ......................................... 604/180; 604/174
[58] Field of Search .................................. 604/258, 259, 604/173, 174, 178, 179; 128/DIG. 26

[56] References Cited

U.S. PATENT DOCUMENTS

| | | | |
|---|---|---|---|
| 2,727,512 | 12/1955 | Muller | 128/DIG. 26 X |
| 2,727,513 | 12/1955 | Muller | 128/DIG. 26 X |
| 3,059,645 | 10/1962 | Hasbrouck et al. | 128/DIG. 26 X |
| 3,696,920 | 10/1972 | Lahay | 128/DIG. 26 X |
| 4,480,639 | 11/1984 | Peterson et al. | 128/DIG. 26 X |
| 4,605,397 | 8/1986 | Ligon et al. | 128/DIG. 26 X |
| 4,797,429 | 1/1989 | Feldstein | 604/174 |
| 5,336,179 | 8/1994 | Ryan | 604/258 |

*Primary Examiner*—Sam Rimell
*Attorney, Agent, or Firm*—Kenneth W. Float

[57] ABSTRACT

Apparatus for securing one or more suction tubes, hoses, and electrical and/or endoscopic cables during an operation. The apparatus is a surgical attachment device that includes a slightly flexible member (flexible plastic, for example) having one or more grooves formed therein. A first portion or tunnel of each groove is dimensioned to slidably secure the respective tube, hose, or cable. A second portion of each groove, superficial to the first portion, is slightly narrower than the first portion of each groove. This configuration allows for insertion of the tube, hose, or cable into the tunnels, which is done by transiently deforming the narrower portion of the groove, deforming the tube, hose, or cable, or both, and pushing the tube, hose, or cable into the tunnel. A second embodiment of the apparatus include selected additional lower grooves separated from the grooves by hinge areas that permit easy flexing of the flexible member and opening of the grooves to permit insertion of the tubes, hose, or cables. Once the tube, hose, or cable is within its tunnel, the narrower portion of the groove restricts unintended pull-out of the tube, hose, or cable from the attachment device. The length of the tunnels and the relative dimensions of the tube/hose/cable to their tunnels determines the drag coefficient as they are pulled through the tunnels. These proportions are designed to provide for intentional sliding through the tunnels, and also provide sufficient friction to resist most unwanted motion. Each groove may be flared at their ends. In the case of the suction tube, this flaring allows the tube to undergo angular movement without compromising the internal geometry of the tube. An adhesive layer is disposed on the second surface of the flexible member so that it may be secured during an operation.

13 Claims, 2 Drawing Sheets

SURGICAL ATTACHMENT DEVICE

CROSS REFERENCE TO RELATED APPLICATIONS

This application is a continuation of U.S. patent application Ser. No. 08/369,010, filed Jan. 5, 1995 now abandoned.

BACKGROUND

The present invention relates generally to medical equipment, and more particularly, to a surgical attachment device that is used to secure cables and tubing during an operation.

During surgical operations, it is customary for surgeons and other operating room personnel to employ suction tubes to remove blood, tissue and other cellular debris from a patient that is undergoing an operation, and air-driven pneumatic tools that are driven by an air source(s) coupled to the tools by way of pneumatic hoses. Furthermore, it is customary to use electrosurgical instruments that are used to as cutting and coagulation tools during surgery. These electrosurgical instruments are connected to electrical equipment by way of electrical cables. Unipolar electrosurgical instruments transmit current through the patient to a grounding pad, while bipolar electrosurgical instruments transmit current between the two heads of bipolar forceps. Such electrosurgical instruments, pneumatic tools, and cables are used in almost all surgeries.

During surgery, it is common practice to store the electrosurgical instruments and tools in a self-adherent plastic pocket of a drape that is disposed over the patient when they are not in use. This also provides easy access for the surgeon. The cables and hoses that connect the electrosurgical instruments and tools to their electrical equipment and air sources are loosely gathered together adjacent an extremity of the patient and are secured by wrapping a portion of the drape around the cables and then holding them in place using a surgical clamp. In a similar fashion, the suction tubes are also routed and clamped in place, typically by the same type of surgical clamp. As should be clear from this typical operating room scenario, the cables are not very well controlled and in many instances interfere with the operation, or may become dislodged or contaminated.

Accordingly, and in order to overcome the limitations of conventional operating room practices, it is an objective of the present invention to provide for a surgical attachment device that is used to secure tubes and electrical cables during an operation.

SUMMARY OF THE INVENTION

In order to meet the above and other objectives, the present invention is a surgical attachment device for securing one or more cylindrically shaped members, including tubes and/or cables, such as suction tubes, hoses, and electrical cables during an operation. The surgical attachment device comprises a flexible member having at least one groove formed therein adjacent one surface thereof. A first portion of each groove is dimensioned to slidably secure the cylindrically shaped member, such as a suction tube, hose, or unipolar, bipolar, or endoscopic cable, for example. A second portion of each groove immediately adjacent the first surface is dimensioned to be slightly smaller than the dimension of the first portion of the groove. The flexible member is flexible or deformable adjacent the second portion of each groove to permit passage of the cylindrically shaped member through the second portion of the groove and into the first portion of the groove. Each groove may be tapered at one end to assist in securing the cylindrically shaped member therein and to prevent unwanted sliding thereof. An adhesive layer is disposed on the second surface of the flexible member so that it may be secured to the surgical drape during an operation. A modification of the surgical attachment device includes the use of additional lower grooves separated from selected grooves by hinge areas that permit easy flexing of the flexible member and opening of the grooves to permit insertion of the tubes, hose, or cables.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
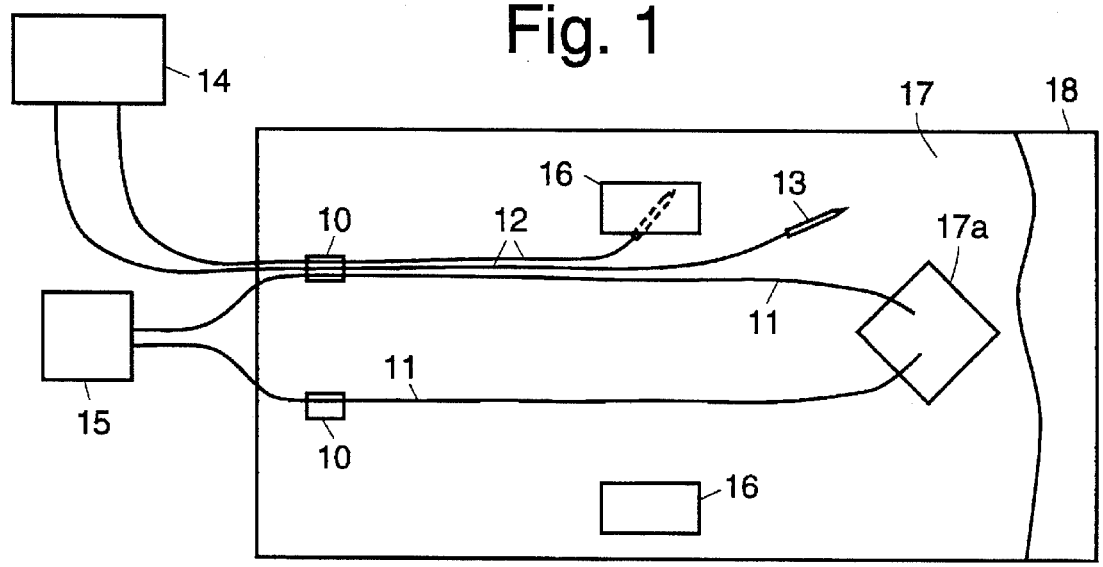
FIG. 1 shows a typical operating room scenario employing surgical attachment devices in accordance with the principles of the present invention.

Referring to the drawing figures, FIG. 1 shows a typical operating room scenario employing surgical attachment devices 10 in accordance with the principles of the present invention. FIG. 1 shows an operating room table 18 on which is disposed a surgical drape 17 the is used to cover a patient (not shown) during an operation. The drape has an opening 17a therein that exposes an area of the patient that is to be operated on. Self-adhering plastic pockets 16 are attached to the drape 17 in which surgical instruments 13 may be stored when not in use. Typical surgical instruments 13 include electrosurgical instruments 13 used for cutting and coagulation of tissues, endoscopic instruments 13 used for minimally invasive surgery in various body cavities, or pneumatic air-driven instruments 13 of all types.

The surgical instruments 13 are connected to electrical equipment 14 (controller 14) in a conventional manner by means of unipolar and bipolar electrical cables 12 for the cauterizing instruments 13, endoscopic cables 12 for the endoscopic instruments 13, and hoses for the pneumatic air-driven instruments 13. In addition, suction tubes 11 are coupled to vacuum equipment 15 and are used to remove blood, tissue and other cellular debris from the patient during the operation.

Figure 2:
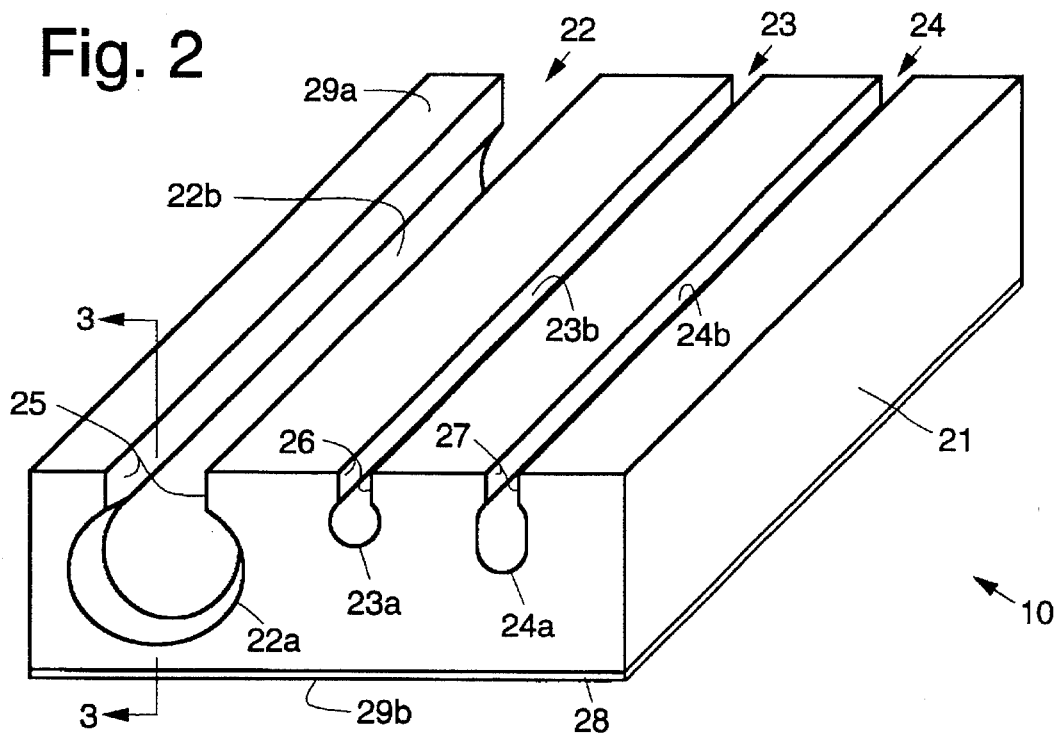
FIG. 2 is a perspective view of an embodiment of the surgical attachment device of the present invention.

The surgical attachment devices 10 of the present invention is used to secure the respective suction tubes 11 and electrical or endoscopic cables 12 in an orderly manner during the operation. Referring to FIG. 2, it shows a perspective view of a typical embodiment of the surgical attachment device 10 in accordance with the principles of the present invention. It is to be understood that the surgical attachment device 10 shown in FIG. 2 is illustrative of one of the many embodiments thereof that may be provided using the principles of the present invention.

More specifically, the surgical attachment device 10 is comprised of a flexible member 21 that may be a block of flexible or deformable plastic, such as polyethylene or polystyrene, for example. The surgical attachment device 10 and flexible member 21 may have a length of about 50 millimeters, a width of about 40 millimeters, and a thickness of about 15 millimeters, for example. The surgical attachment device 10 has at least one, and in a preferred embodiment, three grooves 22, 23, 24 formed adjacent a first surface 29a thereof. Each of the grooves 22, 23, 24 is sized to secure a particular suction tube 11 or cable 12 therein. It is to be understood that while the embodiment shown in FIG. 2 illustrates grooves 22, 23, 24 for use with suction tubes 11 and cables 12, the sizing and number of grooves 11, 12 may be altered to meet particular requirement for different sized tubes 11 and cables 12. Consequently, the embodiment of the surgical attachment device 10 shown in FIG. 2 should not be taken as limiting.

With respect to the grooves 22, 23, 24 shown in the embodiment of FIG. 2, the first groove 22 is sized for use with the suction tube 11 and has a first portion 22a, or tunnel 22a, that may have a diameter of about 10 millimeters, for example. A second portion 25 of the first groove 22 comprises an opening 22b that has a dimension that is smaller than the diameter of the first portion 22a, or tunnel 22a, and which may be on the order of 7 millimeters, for example. The second groove 23 is sized for use with a unipolar electrical cable 12 and has a first portion 23a, or tunnel 23a, that may have a diameter of about 3 millimeters, for example. A second portion 26 of the second groove 23 comprises an opening 23b that has a dimension that is smaller than the diameter of the first portion 23a, or tunnel 23a, and which may be on the order of 2.9 millimeters, for example. The third groove 24 is sized for use with a bipolar electrical cable 12 and has a first portion 24a, or tunnel 24a, that may have a cross section of about 2 millimeters by about 4 millimeters, for example. A second portion 27 of the third groove 23 comprises an opening 24b that has a dimension that is smaller than the diameter of the first portion 24a, or tunnel 24a, and which may be on the order of 1.9 millimeters, for example.

An adhesive layer 28 is disposed on a second surface 29b of the flexible member 21 so that it may be secured to the surgical drape 17 during an operation. The adhesive layer 28 may be comprised of any suitable adhesive, such as those commonly used in medical applications. The adhesive layer 28 is affixed or otherwise coated onto the second surface 29b of the flexible member 21 and a backing layer (not shown) such as is provided by wax-coated paper, for example, may be applied to the exposed surface of the adhesive layer 28. The backing layer is used to cover the adhesive layer 28 prior to use, and is peeled off to expose the adhesive layer 28, whereafter the surgical attachment device 10 is then secured to the drape 17.

Figure 3:
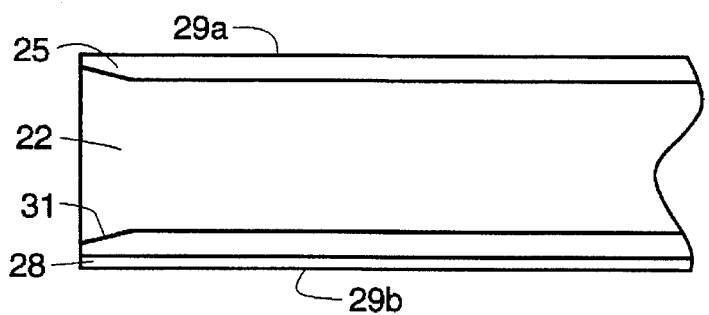
FIG. 3 is a cross sectional view of the surgical attachment device of FIG. 2 taken along the lines 3—3 in FIG. 2

Referring to FIG. 3, it shows a cross sectional view of the surgical attachment device 10 shown in FIG. 2 taken along the lines 3—3. The first groove 22 may have flared ends 31 (although only one end is shown). Such flared ends 31 allow for angular movement of the tube 11 before it becomes kinked or deformed, thus minimizing the possibility of flow restriction within the tube 11 due to altering the internal geometry of the tube 11.

Due to the coincident sizes of the tunnel 22a, 23a, 24a formed within the flexible member 21 (plastic block) and the cables 12, hose, or tube 11 passing through them, a certain amount of friction is produced. The length of the tunnels 22a, 23a, 24b, in part, determines the friction or drag that is encountered by the tube 11 or cables 12 passing through the flexible member 21, when they are pulled or pushed through their respective tunnels 22a, 23a, 24a. The length of the tunnels 22a, 23a, 24a, the relative diameters of the tunnels 22a, 23a, 24a, and the tube 11, hose, or cables 12 passing through them, are proportioned to provide optimal control of the tube 11 and cables 12. The narrowed surface entry zones created at the flared ends 31 are sufficient to prevent easy pull-out of the tubes 11 or cables 12, while easily allowing insertion of the tube 11 or cables 12 into their respective tunnels 22a, 23a, 24a.

In operation, the tubes 11 or cables 12 are inserted into the tunnels 22a, 23a, 24a by transiently deforming the narrower portion of each groove 22, 23, 24, deforming the tube 11, hose, or cable 12, or both, and pushing the tube 11, hose, or cable 12 into the tunnel 22a, 23a, 24a. Once the tube 11 or cable 12 is within its tunnel 22a, 23a, 24a, the narrower portion of the groove 22, 23, 24 restricts unintended pull-out of the tube 11 or cables 12 from the attachment device 10. The length of the tunnels 22a, 23a, 24a and the relative dimensions of the tubes/cables/hoses 11, 12 to their tunnels determines the drag coefficient as they are pulled through the tunnels 22a, 23a, 24a. These proportions are designed to provide for intentional sliding through the tunnels 22a, 23a, 24a, and also provide sufficient friction to resist most unwanted motion. The grooves 22, 23, 24 may be flared at their ends. In the case of the suction tube 11, for example, this flaring allows the tube 11 passing through its tunnel 24a to move angular without compromising the internal geometry of the tube 11.

The surgical attachment device 10 may be manufactured by molding or machining the flexible member 21 to form the grooves 22, 23, 24. The adhesive layer 28 is then coated or disposed on the second surface 29b of the flexible member 21 and the backing layer is applied to the exposed surface of the adhesive layer 28. This assembly is then packaged and the packaged assembly is sterilized by means of gamma radiation sterilization procedures commonly used in the medical industry. During an operation, the sterilized package is opened, the surgical attachment device 10 is removed from the package. The backing layer is removed from the surgical attachment device 10 to expose the adhesive layer 28, and the surgical attachment device 10 is secured to the surgical drape 17, for example, in an appropriated place relative to the location of the surgery. The suction tube 11, hoses, and cables 12 are then inserted into the respective grooves 22, 23, 24 to hold them in place during the surgery.

Figure 4:
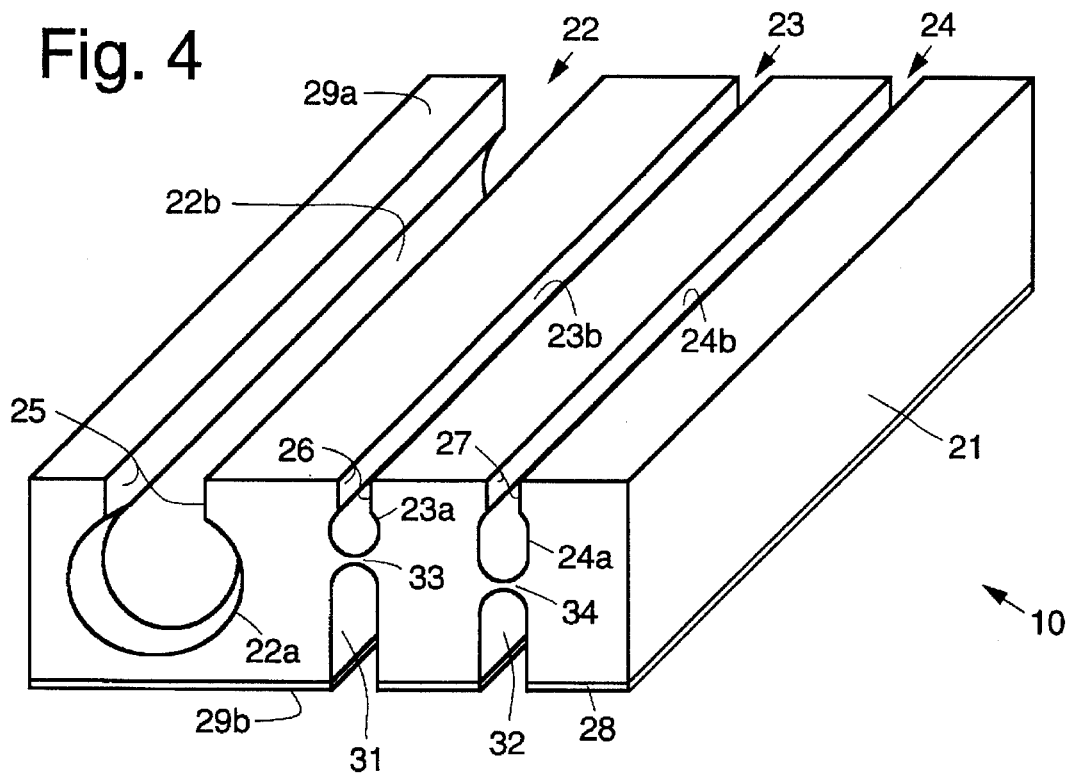
FIG. 4 is a perspective view of a second embodiment of the surgical attachment device of the present invention.

Referring to FIG. 4, it shows a perspective view of a second embodiment of the surgical attachment device 10. This second embodiment is substantially identical to the first embodiment but is additionally designed to more easily insert the cables 12 into the tunnels 23a, 23b of the grooves 23, 24. In this second embodiment, the surgical attachment device 10 further includes a plurality of lower grooves 31, 32 formed adjacent the second surface of the flexible member 21 that are separated from the respective tunnels 23a, 23b by means of hinge areas 33, 34. The lower grooves 31, 32 extend the entire length of the flexible member 21. The lower grooves 31, 32 and hinge areas 33, 34 permit flexing of the flexible member 21 so that the respective grooves 23, 24 for the cables 12 open to permit insertion of the cables 12 therein. This will be explained more clearly with respect to FIGS. 5a and 5b.

Figure 5A:
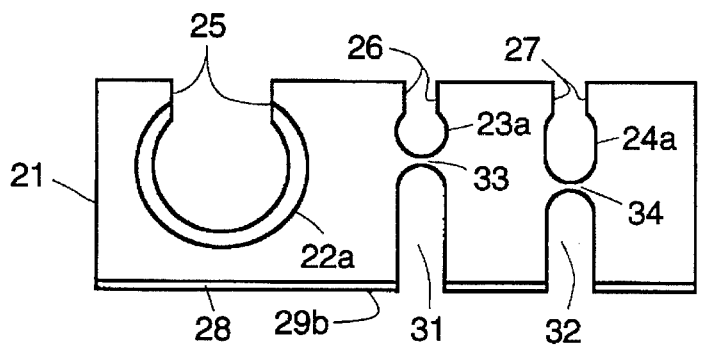
FIG. 5a is an end view of the device of FIG. 4.
Figure 5B:
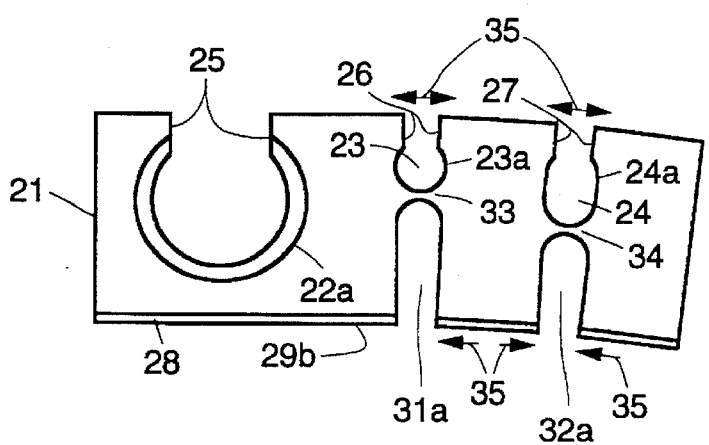
FIG. 5b is an end view of the device of FIG. 5a in a flexed condition.

FIG. 5a is an end view of the surgical attachment device shown in FIG. 4, while FIG. 5b is an end view of this surgical attachment device 10 in a flexed condition. The arrows 35 in FIG. 5b illustrate the relative motion of the edges of the respective grooves 23, 24, 31, 32. As can be seen in FIG. 5b, the flexible member 21 may be flexed by bending it so that the lower ends of the lower grooves 31, 32 are made to move closer together, which causes the grooves 23, 24 or tunnels 23a, 24a to expand adjacent their respective opening to permit ease of insertion of the cables therein. It is to be understood that the use of the lower groove 31, 32 may be applied to any or all of the respective grooves 22, 23, 24, depending upon the configuration of the flexible member 21 and the types of cylindrical members (tubes 11 or cables 12) that are to be secured therein.

Thus there has been described a new and improved surgical attachment device that is used to secure suction tubes and electrical cables during an operation. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. Apparatus comprising:
    a single flexible member having first and second surfaces and having a plurality of grooves formed adjacent the first surface that each extend from one lateral side of the flexible member to an opposite lateral side thereof such that distal ends of the grooves adjacent the lateral sides of the flexible member are open, and wherein a first portion of each groove has a predetermined cross section for slidably securing a corresponding cylindrically shaped member therein, and wherein a second portion of each of the grooves disposed immediately adjacent the first surface is slightly smaller than the respective first portion of each of the grooves, and wherein the single flexible member comprises a plurality of lower grooves formed adjacent the second surface that are separated from respective first portions of the plurality of grooves by a plurality of hinge areas, and wherein the single flexible member is flexible at each of the hinge areas to permit opening of the grooves and passage of the cylindrically shaped members through the second portions of the grooves and into the first portions thereof secure of the cylindrically shaped members therein; and
    an adhesive layer disposed on the second surface of the flexible member.

2. The apparatus of claim 1 wherein at least one of the grooves is flared at the distal ends thereof adjacent the lateral sides of the flexible member.

3. A device for securing a suction tube and first and second cables to a surgical drape during an operation, and wherein the suction tube and first and second cables respectively have first, second and third predetermined cross-sections, said device comprising:
    a single flexible member having first and second surfaces and having a plurality of grooves formed therein adjacent the first surface that each extend from one lateral side of the flexible member to an opposite lateral side thereof such that distal ends of the grooves adjacent the lateral sides of the flexible member are open, and wherein a first portion of each respective groove has a cross-section that is approximately the same as the respective cross-sections of the suction tube and first and second cables, respectively, so that they are slidably securable therein, and wherein a second portion of each of the grooves disposed immediately adjacent the first surface is slightly smaller than the respective first portion of each of the grooves, and comprising a plurality of lower grooves formed adjacent the second surface that are separated from respective first portions of the grooves by a plurality of hinge areas, and wherein the flexible member is flexible at each of the hinge areas to permit opening of the grooves and passage of the suction tube and first and second cables through the second portions of the grooves, respectively, and into the first portions of the grooves to permit securing of the suction tube and first and second cables therein; and
    an adhesive layer disposed on the second surface for securing the single flexible member to the surgical drape during an operation.

4. The device of claim 3 wherein at least one of the grooves is flared at the distal ends thereof adjacent the lateral sides of the flexible member.

5. The device of claim 3 wherein one of the grooves has a cross-section sized to secure a unipolar cable therein.

6. The device of claim 3 wherein one of the grooves has a cross-section sized to secure a bipolar cable therein.

7. The device of claim 3 wherein the one of the grooves has a cross-section sized to secure an endoscopic cable therein.

8. Apparatus comprising:
    a rectangular block of plastic having first and second surfaces and having a groove formed therein adjacent the first surface that extends from one lateral side of the rectangular block of plastic to an opposite lateral side thereof such that distal ends of the groove adjacent the lateral sides of the rectangular block of plastic is open, and wherein a first portion of the groove has a cross section for slidably securing a cylindrically shaped member therein, and wherein a second portion of the groove disposed immediately adjacent the first surface is slightly smaller than the first portion of the groove, and wherein the rectangular block of plastic comprises a lower groove formed adjacent the second surface that is separated from the first portion of the groove by a hinge area, and wherein the block of plastic is flexible at the hinge area to permit opening of the groove and passage of the cylindrically shaped member through the second portion of the groove and into the first portion thereof to secure of the cylindrically shaped member therein; and
    an adhesive layer disposed on the second surface of the rectangular block of plastic.

9. The apparatus of claim 8 wherein the groove is flared at the distal ends thereof adjacent the lateral sides of the rectangular block of plastic.

10. The apparatus of claim 8 wherein rectangular block of plastic comprises polyethylene.

11. The apparatus of claim 8 wherein rectangular block of plastic comprises polystyrene.

12. The apparatus of claim 9 wherein rectangular block of plastic comprises polyethylene.

13. The apparatus of claim 9 wherein rectangular block of plastic comprises polystyrene.

* * * * *